(12) United States Patent
Heuwes et al.

(10) Patent No.: US 9,340,480 B2
(45) Date of Patent: May 17, 2016

(54) ALDEHYDE PRODUCTION PROCESS WITH MULTI-STAGE CONDENSATION

(71) Applicant: Oxea Corporation, Dallas, TX (US)

(72) Inventors: Markus Heuwes, Sargent, TX (US); Bakulesh N. Shah, Bay City, TX (US)

(73) Assignee: OXEA CORPORATION, Dallas, TX (US)

( * ) Notice: Subject to any disclaimer, the term of this patent is extended or adjusted under 35 U.S.C. 154(b) by 0 days.

(21) Appl. No.: 14/782,694

(22) PCT Filed: Nov. 11, 2013

(86) PCT No.: PCT/US2013/069382
§ 371 (c)(1),
(2) Date: Oct. 6, 2015

(87) PCT Pub. No.: WO2014/178912
PCT Pub. Date: Nov. 6, 2014

(65) Prior Publication Data
US 2016/0068460 A1    Mar. 10, 2016

Related U.S. Application Data

(60) Provisional application No. 61/817,506, filed on Apr. 30, 2013.

(51) Int. Cl.
| | | |
|---|---|---|
| C07C 45/00 | (2006.01) | |
| B01D 53/00 | (2006.01) | |
| C07C 45/78 | (2006.01) | |
| C07C 45/50 | (2006.01) | |
| C07C 45/81 | (2006.01) | |

(52) U.S. Cl.
CPC ............ C07C 45/783 (2013.01); B01D 53/002 (2013.01); C07C 45/505 (2013.01); C07C 45/81 (2013.01)

(58) Field of Classification Search
CPC .... C07C 45/81; C07C 45/505; C07C 45/783; B01D 53/60
USPC .......................................... 568/492; 422/187
See application file for complete search history.

(56) References Cited

U.S. PATENT DOCUMENTS

| | | |
|---|---|---|
| 4,148,830 A | 4/1979 | Pruett et al. |
| 4,593,127 A | 6/1986 | Bunning et al. |
| 5,105,018 A | 4/1992 | Miyazawa et al. |
| 5,648,553 A | 7/1997 | Ueda et al. |
| 5,770,021 A | 6/1998 | Hego et al. |

FOREIGN PATENT DOCUMENTS

| | | |
|---|---|---|
| CN | 202148269 U | 2/2012 |
| EP | 0751110 A1 | 1/1997 |

OTHER PUBLICATIONS

International Search Report dated Feb. 19, 2014.

*Primary Examiner* — Sikarl Witherspoon
(74) *Attorney, Agent, or Firm* — Michael W. Ferrell

(57) ABSTRACT

A hydroformylation system for making aldehyde by reacting olefin with synthesis gas by way of hydroformylation is improved by multi-stage condensation of gaseous reactor effluent for providing liquid feed to a gas-liquid contact zone. The process provides for condensing and separating the gaseous reactor output stream in a plurality of successive condenser stages into gaseous condenser output streams and liquid condenser output streams having differing temperatures and feeding the recovered liquid to the gas-liquid contact zone to improve olefin recovery by stripping.

20 Claims, 3 Drawing Sheets

ALDEHYDE PRODUCTION PROCESS WITH MULTI-STAGE CONDENSATION

CLAIM FOR PRIORITY

This application is a National Phase Application of International Patent Application No. PCT/US2013/069382, filed Nov. 11, 2013 which was based upon U.S. Provisional Application No. 61/817,506 filed on Apr. 30, 2013. The priorities of International Patent Application No. PCT/US2013/069382 and U.S. Provisional Application No. 61/817,506 are hereby claimed and their disclosures incorporated herein by reference.

TECHNICAL FIELD

The present invention relates to aldehyde production by way of hydroformylation with multi-stage condensing of reactor effluent to control feed temperature to an olefin recovery column without the need for reheating a product stream.

BACKGROUND

Processes for hydroformylating an olefin to prepare a carbonyl derivate containing one carbon atom more than the starting olefin by reacting the olefin with carbon monoxide and hydrogen, which mixture is also called synthesis gas, in the presence of a Group VIII metal, e.g., rhodium, in complex combination with an organic ligand and carbon monoxide also being a component of the catalyst complex, are well known in the art (referred to sometimes as "OXO" processes) and have enormous industrial importance. The hydroformylation of olefins can be conducted in mode of the "liquid recycle process" where the product is recovered in liquid form, see U.S. Pat. No. 4,148,830 or in the process mode of the "gas recycle process" according to U.S. Pat. No. 4,593,127. According to the gas recycle process mode, synthesis gas and olefin are sparged through the liquid reaction mixture and the gas stream taken from the hydroformylation reaction zone contains the desired aldehydes in addition to unreacted olefin and synthesis gas. Because substantial amounts of the unreacted olefins are dissolved in the product streams taken from the hydroformylation reactor, the art discloses several techniques to recover said valuable olefin and to recycle it to the main hydroformylation reaction zone and, occasionally, to use it in a vent hydroformylation reaction zone.

According to U.S. Pat. No. 5,367,106 the gaseous effluent vented from the primary process is condensed in a heat exchanger and the uncondensed gas and liquid are separated in a gas-liquid separator. The non-condensed vent gases containing unreacted olefin and synthesis gas from the gas-liquid separator are then introduced into a secondary hydroformylation reactor. It is a characteristic feature of the process of U.S. Pat. No. 5,367,106 that the solubilized rhodium-phosphorus complex catalyst is circulated between said primary and secondary process.

U.S. Pat. No. 5,105,018 likewise discloses a two-stage reactor system in the hydroformylation of olefins. The gaseous reactor effluent is cooled to 70° C. and then subjected to a gas-liquid separator. The gaseous product from the gas-liquid separator is partially returned to the first reactor stage, while the other portion is fed to a second reactor stage, acting as a vent reactor. The liquid formed in the gas-liquid separator after cooling and which contains a substantial amount of unreacted olefin is then subjected to a gas-liquid contact zone, also known in the art as a gas-liquid stripping zone, where the liquid is countercurrently contacted with carbon monoxide and hydrogen in order to strip unreacted olefin from the product. The recovered olefin from this operation is recycled to the first reactor system.

According to U.S. Pat. No. 5,648,553 the gas stream withdrawn from the hydrofromylation reaction zone is cooled to 40° C. and the liquid formed is heated again using a heat exchanger. After adjusting the temperature the liquid is provided to a gas-liquid contact zone in order to recover unreacted olefin from the liquid stream. The separation efficiency of the unreacted olefin can be improved by heating the feed temperature of the liquid feed to the gas-liquid contact zone.

Also noted is Chinese Patent Publication CN 20214826 which discloses a system for separating organic phases in stages in in connection with a hydroformylation reaction.

Thus, the art teaches a one-stage cooling step of the reactor effluent or an additional heating step of heating the cooled liquid process stream obtained down-stream from the gas-liquid separator before entering into gas-liquid contact zone. Significant drawbacks of one-stage cooling is that large amounts of product aldehyde is recycled and/or the product stream contains large amounts of olefin that cannot be efficiently removed in the gas-liquid contact zone. Reheating condensate, on the other hand, adds additional costs for equipment and energy.

SUMMARY OF INVENTION

The invention relates to a method for producing aldehydes which comprises reacting an olefin with carbon monoxide and hydrogen in a hydroformylation reaction zone in the presence of a rhodium catalyst having an organophosphorus compound as ligand, removing the reaction products from the hydroformylation reaction zone in the form of a gas stream, condensing the gas stream in two or more stages at various temperatures to form various liquid streams having various temperatures and supplying the liquid streams to a gas-liquid contact zone where the liquid is countercurrently contacted with carbon monoxide and hydrogen. A gas stream comprising carbon monoxide, hydrogen and unreacted olefin is withdrawn from the gas-liquid contact zone to separate and recover the unreacted olefin. The recovered unreacted olefin is typically recycled together with the carbon monoxide and hydrogen to the hydroformylation reaction zone.

It has been found that the use of a multi-stage condensation process at various temperatures at or above ambient and below reaction temperature provides a substantial improvement with regard to the recovery of the olefin dissolved in the liquid stream obtained from the gas-liquid separator downstream to the hydroformylation reaction zone. In the multi-stage condensation process of the invention, the condensed liquid streams resulting from each condensation step are then preferably combined for ease of handling and fed to the gas-liquid contact zone for the recovery of the olefin. This multi-stage condensation process allows to adjust the feeding temperature of the liquid feed to the gas-liquid contact zone without additional heating as proposed in the art. It is advisable to feed the vapor stream from the first condensation stage, which has the highest temperature, to a vent reactor for best heat recovery. The vapor stream from the last condensation stage, which is the coldest, is sent to the recycle gas compressor from where the gaseous stream is recycled to the main hydroformylation reaction zone.

In theory, an infinite number of condensation stages will achieve the highest possible feed temperature. However, as a practical matter the multi-stage condensation process is operated as a two-stage to four-stage, in particular as a two-stage condensation process.

Another benefit of the invention is that the invention enables a lower recycle gas compressor suction temperature which allows for increased production at a fixed compressor power demand as less product aldehyde is recycled via the recycle gas compressor as will be appreciated from the discussion which follows.

The present invention is particularly useful for the hydroformylation of propylene to produce n-butyraldehyde and iso-butyraldehyde as well as for the hydroformylation of ethylene to make propionaldehyde.

BRIEF DESCRIPTION OF DRAWINGS

The invention is described in detail below with reference to the drawings wherein like numerals designate similar parts. In the drawings.

DETAILED DESCRIPTION

Figure 1:
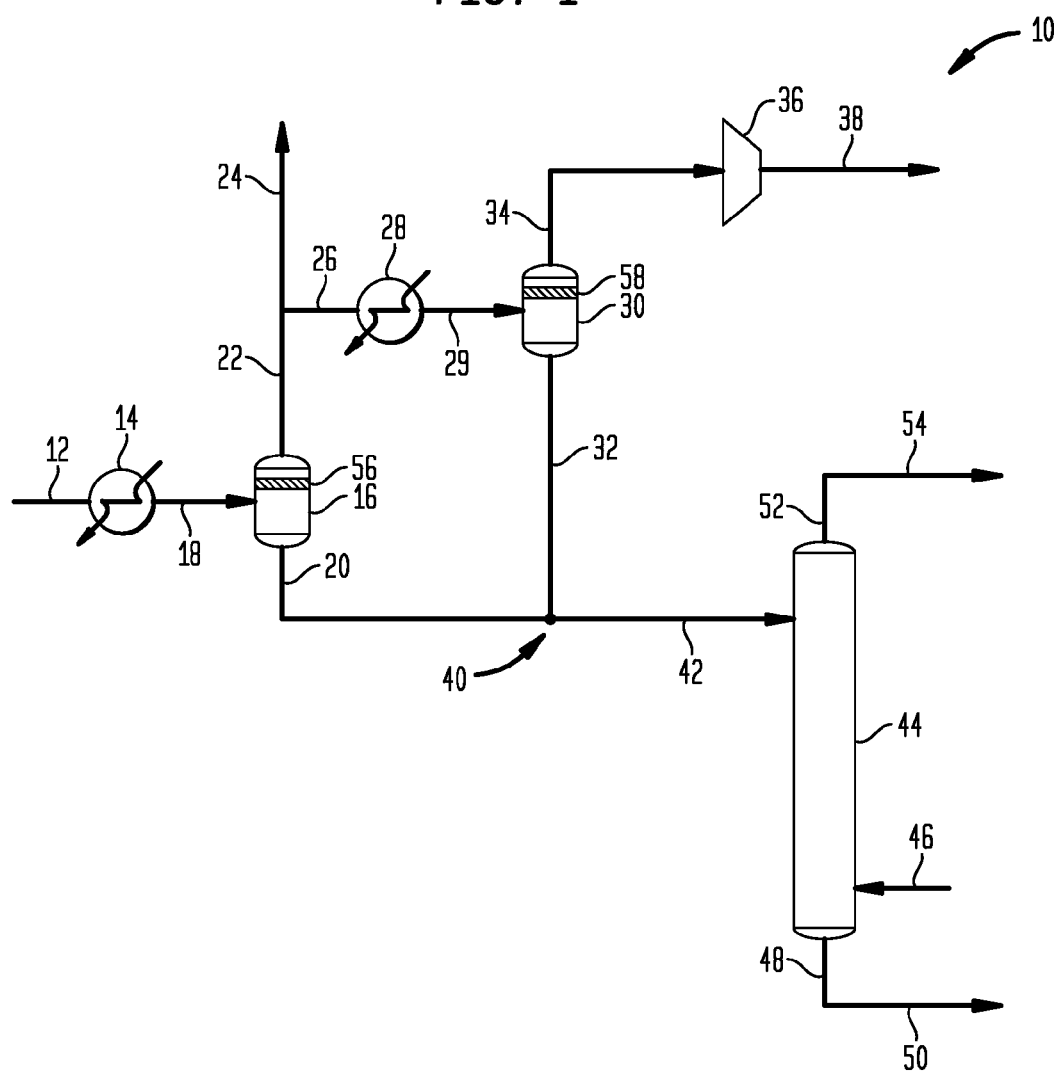
FIG. 1 is a schematic diagram illustrating two-stage condensation and olefin stripping of a gaseous stream received from a hydroformylation reactor.

The invention is described in detail below in connection with the Figures for purposes of illustration, only. The invention is defined in the appended claims. Terminology used throughout the specification and claims herein are given their ordinary meanings; for example "duct", "line" and similar terminology refers to any tube, canal, pipe, valve or conduit by which a fluid, air, or other substance is conducted or conveyed. "Stream" refers to the flowing contents of a duct or line as will be apparent from the discussion which follows.

"Liquid feed" temperature and like terminology refers to the temperature of a feed stream generated by combining liquid output from a plurality of condenser stages, or refers to the weighted temperature of the feed provided to a gas-liquid contact zone if liquid feed is provided to the gas-liquid contact zone in more than one stream. For example, if a liquid stream at a temperature, $T_1$, is fed to a stripper column at a flow rate, $W_1$ along with a separate liquid stream at a temperature of $T_2$ at a flow rate of $W_2$, the liquid feed temperature T is approximately=

$$\frac{T_1 W_1}{(W_1 + W_2)} + \frac{T_2 W_2}{W_1 + W_2)}$$

The calculated value of T is approximate due to slight variation in heat capacity. The olefin content of the feed is similarly calculated if the liquid feed streams are not combined prior to feeding to the gas-liquid contact zone.

As used herein, a "condenser stage" refers to an assembly adapted to receive a gaseous stream as input and generate both a liquid stream and a gaseous stream as outputs. A condenser stage may include, for example, both a cooler and separator vessels or combine the features in a single vessel. Unless otherwise indicated, liquid temperatures in the cooler, separator and as fed to the gas-liquid contact zone, are essentially the same.

The present invention relates to hydroformylation, often referred to in the art as the OXO process whereby aldehydes are prepared via the hydroformylation or OXO reaction, according to which one mol of unsaturated compound is reacted with synthesis gas (syngas) having a molar ratio of hydrogen to carbon monoxide of 1:1 as shown below:

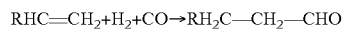

$$RHC=CH_2+H_2+CO \rightarrow RH_2C—CH_2—CHO$$

wherein R is an organic radical. Commercial olefin feedstocks which may be utilized in connection with the present invention are ethylene, propylene, and 1-and 2-butenes, pentenes, hexenes and the like. In general, any suitable olefin having a C2 (ethylene) to C6 (hexene) carbon content may be used. Linear olefins are perhaps most preferred in many embodiments of the present invention. A single methyl branch at the olefinic carbon of a terminal olefin reduces its reaction rate by a factor of ten, but the effect of a branch diminishes as its distance from the double bond increases. Some C6 feedstocks which exhibit different reactivities include: 1-hexene; 4-methyl-1-pentene; 2-hexene; 4-methyl-2-pentene; 2-methyl-1-pentene; 2-methyl-2-pentene; and 2,3-dimethyl-2-butene.

The present invention is especially suited to the "gas recycle process" according to U.S. Pat. No. 4,593,127 noted above, but may be used to process gaseous aldehyde stream with unreacted olefins in connection with other processes. Additional features are seen in U.S. Pat. No. 5,105,018 which discloses a two-stage reactor system in the hydroformylation of olefins. Further details concerning various OXO processes are set forth in *Kirk-Othmer Encyclopedia of Chemical Technology*, $3^{rd}$ Ed., Vol. 11, pp. 637-653 (Wiley, 1980), the disclosure of which is incorporated herein by reference.

Referring to FIG. 1, there is shown schematically a multi-stage liquid recovery system 10 for receiving a product stream 12 from a hydroformylation reactor, typically a gaseous stream; optionally a mixed gas/liquid stream. Stream 12 is fed to a cooler 14 where the effluent is cooled and then provided to a gas/liquid separator 16, sometimes referred to as a knock-out drum, via line 18. In separator 16, the cooled stream is separated into a liquid stream 20 and a gaseous stream 22.

Stream 22 is divided into a vent stream 24 and a second-stage feed stream 26 which is provided to a second cooler 28 via line 26. Stream 24, which includes synthesis gas and unreacted olefin, may be provided to a vent reactor, if so desired, or further processed and optionally recycled.

In cooler 28, stream 26 is cooled and provided to a second-stage separator 30 via line 29 where the cooled stream is separated into a liquid stream 32 and a light ends stream 34. Stream 34 also includes synthesis gas and unreacted olefin and is compressed by compressor 36 and recycled to the hydroformylation reactor via line 38. Due to multi-stage separation, stream 34 is at a lower suction temperature and has lower amounts of product aldehyde than a recycle stream in a conventional gas recycle system. It is accordingly possible in accordance with the invention to increase production at a fixed compressor power demand.

Liquid streams 20, 32 are enriched in the desired aldehyde product and are combined at 40 to form a combined stream 42 which is fed to a stripper column 44 at its upper portion. The product liquid flows downwardly in column 44 while synthesis gas is fed to near the bottom of the column via line 46. Thus, column 44 is operated as a countercurrent gas/liquid stripper column with a gas-liquid contact zone, wherein synthesis gas flows upwardly and the product liquid flows downwardly and exits the column via line 48 as a crude product stream 50.

The synthesis gas is effective to strip unreacted olefin from combined stream 42 and exits the column at line 52 as stream 54, which is enriched in olefin as compare with stream 46. Stream 54 is recycled to the hydroformylation reactor.

Further features of FIG. 1 are optionally provided; for example, separators 16, 30 may be provided with demisters 56, 58 for more efficient separation, if so desired.

In operation, the liquid streams formed in the gas-liquid separator 16 (first-stage) and in the gas-liquid separator 30 (second-stage) are preferably combined before entering the gas-liquid contact zone of column 44, which is operated countercurrently with synthesis gas as is illustrated in FIG. 1. In accordance with the different temperatures in first-stage condenser 14 and separator 16 as compared to second-stage condenser 28 and separator 30, the feeding temperature of the liquid stream to the gas-liquid contact zone of column 44 can be adjusted by controlling temperatures in the streams and combining the streams in order to improve the olefin recovery. Alternatively, the liquid streams from the condenser stages can be fed to the stripper column separately and the liquid feed temperature to the stripper column is the weighted average temperature of the streams and the olefin content is the weighted average olefin content as is noted above. A part of the gaseous stream from gas-liquid separator 16 (first-stage) is preferably fed to a vent reactor while the gaseous stream, from the gas-liquid separator 30 (second-stage) is preferably sent to recycle gas compressor from which the gaseous stream is fed to the main hydrofromylation reaction zone of a hydroformylation system as discussed above.

Table 1 shows the influence of the feed temperature to first gas-liquid separator 16 at a given temperature of the second gas-liquid separator, 130° F. (54° C.) on the combined feeding temperature to the gas-liquid contact zone. As is seen from the data, at a selected combined feeding temperature the olefin content in the crude product stream 50 at the bottom of the stripper (gas-liquid contact zone) can be reduced, without requiring additional heating of the liquid feed to the stripper column.

TABLE 1

Effect of Temperature on Olefin Content of Crude Product Stream

| Liquid Feed Temperature to First-Stage Separator 16° F. (° C.) | Temperature of Combined Liquid Feed to Stripper Column 44 (Stream 42) ° F. (° C.) | g/kg Propylene/ Butyraldehyde in Stream 50 |
|---|---|---|
| 160 (71) | 154.3 (68) | 0.59 |
| 170 (77) | 158.7 (70) | 0.36 |
| 175 (79) | 160.9 (72) | 0.33 |
| 180 (82) | 160.6 (71) | 0.31 |
| 185 (85) | 160.7 (71) | 0.32 |
| 190 (88) | 159.7 (71) | 0.33 |
| 200 (93) | 155.0 (68) | 0.56 |
| 210 (99) | 146.0 (63) | 1.25 |
| 220 (104) | 132.8 (56) | 3.0 |

It will be appreciated from Table 1, where the temperature in the second condenser stage was held at about 54° C., the amount of liquid generated at a higher temperature in the first condenser stage decreased as the first-stage temperature was raised. The pressure employed during the trials was about 22 bar (2.2 MPa) absolute. Preferred temperatures will vary with pressure when practicing the present invention. In general it is readily achievable in accordance with the invention to reduce the olefin content to less than 2 g olefin/kg product aldehyde in the crude product stream. Less than 1 or less than 0.55, 0.45 or 0.35 g olefin/kg product olefin in the crude product stream exiting the stripper is even more preferred.

Figure 2:
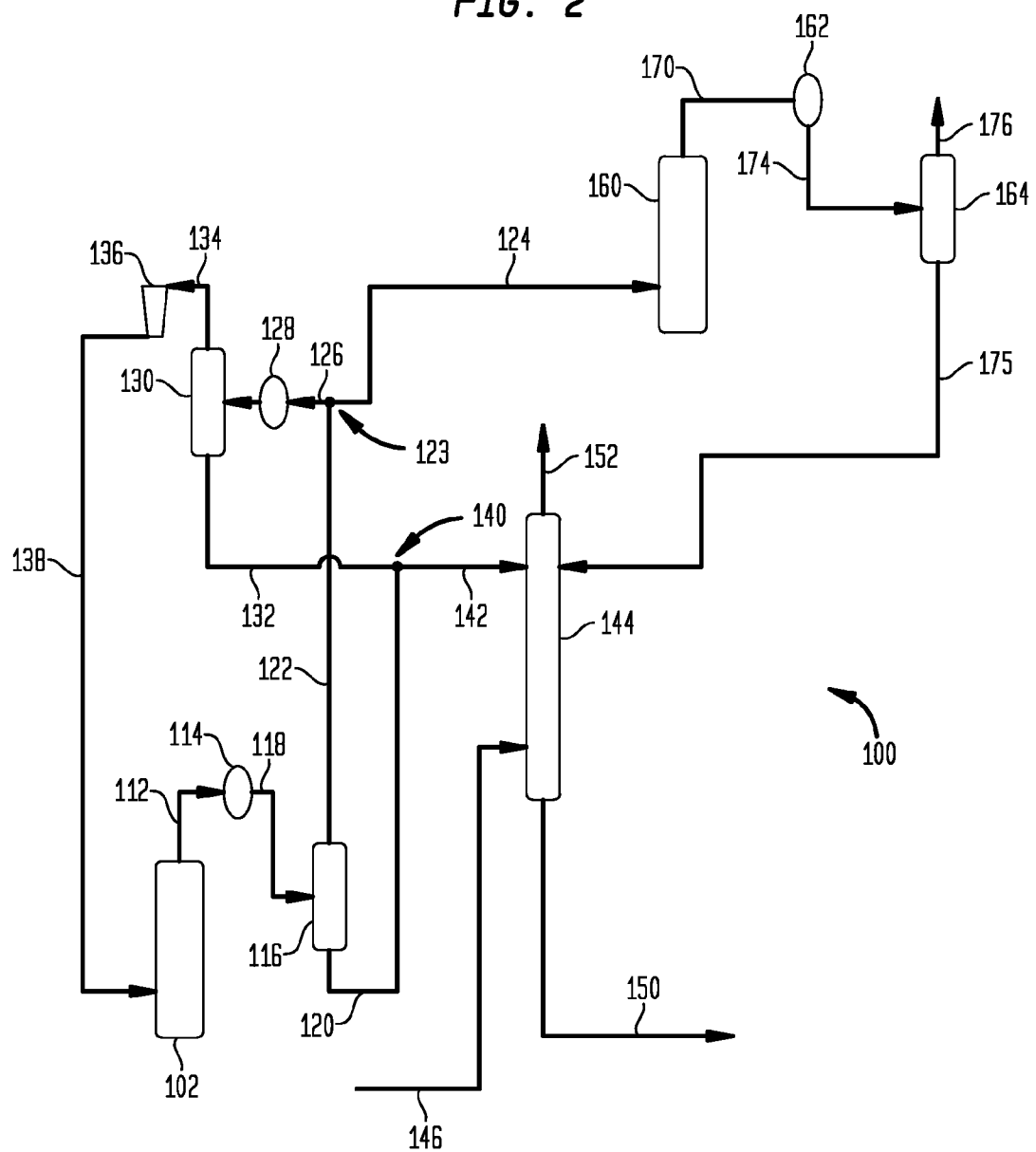
FIG. 2 is a schematic diagram of a hydroformylation production system with a main oxo reactor and a vent oxo reactor provided with two-stage condensation of reactor effluent and olefin stripping and recycle.

Referring to FIG. 2, there is shown schematically an aldehyde production system 100 provided with a main OXO reactor 102, a first-stage condenser 114, a first-stage gas-liquid separator 116, a second-stage condenser 128, a second-stage gas-liquid separator 130, a recycle gas compressor 136, a vent reactor 160, a vent reactor condenser 162 and a vent reactor gas-liquid separator 164.

System 100 may be used to produce butyraldehyde, for example, in accordance with the invention. To this end, catalyst, synthesis gas and propylene are fed to reactor 102 where propylene is converted into butyraldehde with a homogeneous rhodium catalyst as is seen, for example, in U.S. Pat. No. 5,087,763. Reaction product, along with unreacted olefin and synthesis gas, is withdrawn in a gas stream 112 from the overhead space of the reactor and fed to cooler 114 which cools stream 112 and provides an output stream 118 to gas-liquid separator 116. Separator 116 separates stream 118 into a liquid stream 120 and a gaseous stream 122. Stream 120 is enriched in butyraldehyde product, while stream 122 contains higher levels of synthesis gas and unreacted propylene than liquid stream 120.

Stream 122 is optionally divided at 123 into a feed stream 126 for second-stage condenser 128 and a feed stream 124 for vent reactor 160. Stream 126 is cooled and condensed in condenser 128 and provided to second gas-liquid separator 130 which divides the input into a gas stream 134 and a liquid stream 132. Stream 134 is compressed by compressor 136 and recycled to reactor 102 via line 138, while stream 132 is combined with stream 120 at 140 to provide a combined stream 142.

Liquid stream 142 is provided to stripper column 144 countercurrently with a synthesis gas stream 146 which operates to remove unreacted olefin from the butyraldehyde product and exits column 144 in an olefin-enriched gas stream, 152 which is recycled to reactor 102.

In vent reactor 160, unreacted olefin and synthesis gas are reacted in the presence of a suitable catalyst in order to provide another product stream 170 which feeds a condenser 162 which, in turn, feeds another gas-liquid separator 164 via line 174. Separator 164 provides a liquid stream 175 which is fed to column 144 along with stream 142 as shown. Separator 164 also provides a gas stream 176 which includes synthesis gas as well as some unreacted olefin. Stream 176 maybe recycled to reactor 102 or further processed to recover heat or raw material.

A product stream derived from streams 142, 175 with lower levels of unreacted olefins as compared to the feed streams is withdrawn from the bottom of stripper column 144 as crude product stream 150 and further purified by conventional means.

Figure 3:
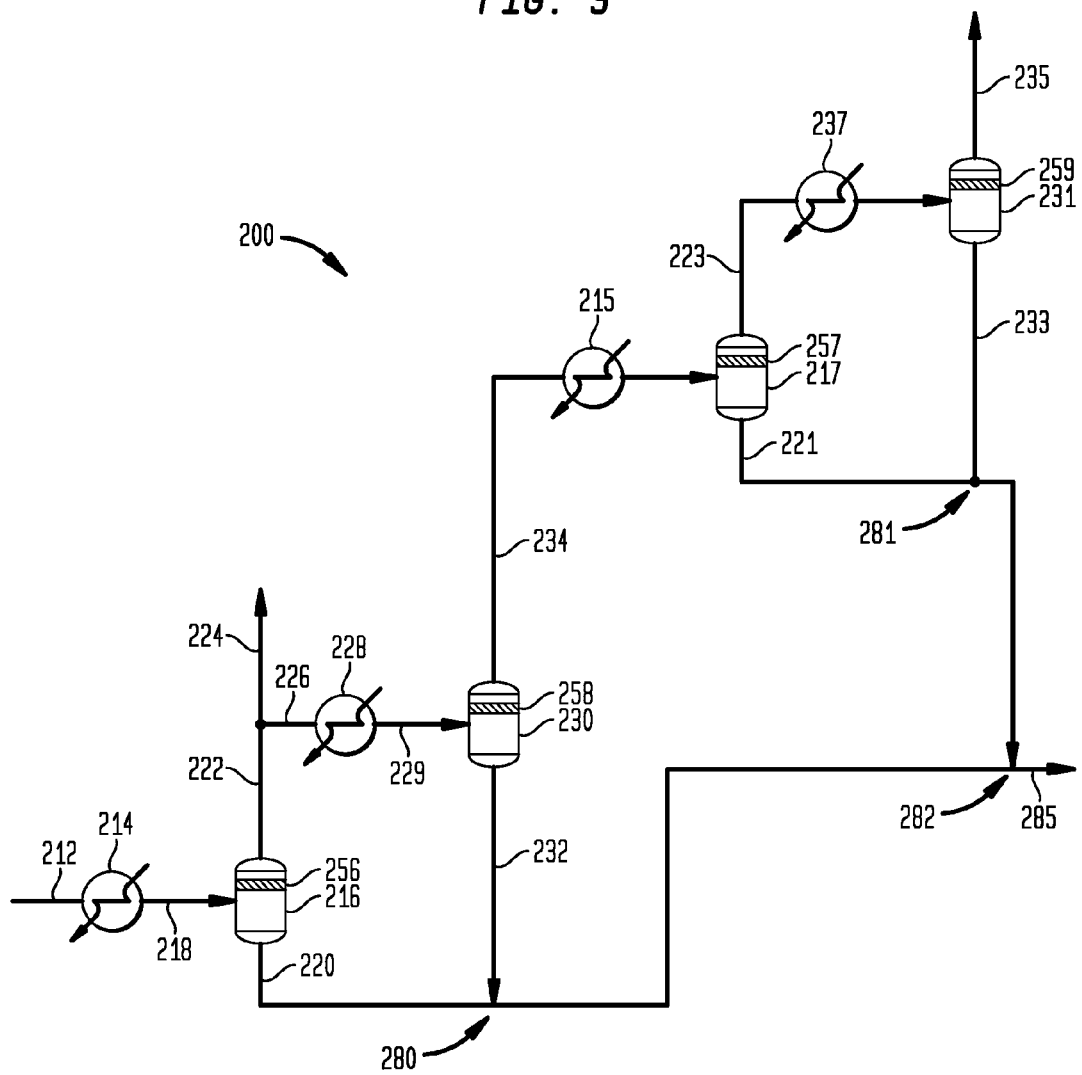
FIG. 3 is a schematic diagram illustrating multi-stage condensation and olefin stripping of a gaseous stream received from a hydroformylation reactor with 4 stages.

Referring to FIG. 3, there is shown schematically a four-stage liquid recovery system 200 for receiving a product stream 212 from a hydroformylation reactor, typically a gaseous stream. The condensing system 200 may be incorporated into the apparatus of FIG. 1 or FIG. 2, that is multi-stage condensation could be applied to the primary hydroformylation overhead and the the vent reactor overhead stream as well. As illustrated in FIG. 3, stream 212 is fed to a cooler 214 where the effluent is cooled and then provided to a gas-liquid separator 216, via line 218. In separator 216, the cooled stream is separated into a liquid stream 220 and a gaseous stream 222. Stream 222 is divided into a vent stream 224 and a second-stage feed stream 226 which is provided to a second cooler 228. In cooler 228, stream 226 is cooled and provided to a second-stage separator 230 via line 229 where the cooled stream is separated into a liquid stream 232 and a light ends stream 234. Stream 234 also includes aldehyde product and unreacted olefin and is fed to a third-stage cooler 215 where the effluent is cooled and then provided to a gas-liquid separator 217. In separator 217, the cooled stream is separated into a liquid stream 221 and a gaseous stream 223.

Stream 223 is fed to a fourth-stage cooler 237. In cooler 237, stream 223 is cooled and provided to a fourth-stage separator 231 where the cooled stream is separated into a liquid stream 233 and a light ends stream 235 which may be recycled to the reactor, if so desired.

Further features of FIG. 3 are optionally provided as well; for example, separators 216, 217, 230 and 231 may be provided with demisters 256, 257, 258 and 259 for more efficient separation, if so desired.

Liquid streams 220, 221, 232 and 233 are enriched in the desired aldehyde product and are combined at 280, 281, and 282 to form a combined stream 285 which is fed to a stripper column at its upper portion, as discussed in connection with FIG. 1 and FIG. 2. The feeding temperature of the liquid stream to the gas-liquid contact zone of the column can be adjusted by controlling temperatures in the streams and combining the streams in order to improve the olefin recovery. Gaseous stream 224 from gas-liquid separator 216 (first-stage) is preferably fed to a vent reactor while gaseous stream 235 from the most down-stream gas-liquid separator 231 is preferably sent to recycle gas compressor from which the gaseous stream is fed to the main hydroformylation reaction zone of a hydroformylation system.

There is thus provided in accordance with the invention a hydroformylation system which is improved by multi-stage condensation of gaseous reactor effluent for providing liquid feed to a gas-liquid contact zone. The process provides for condensing and separating the gaseous reactor output stream in a plurality of successive condenser stages into gaseous condenser output streams and liquid condenser output streams having differing temperatures and combining the liquid condenser output streams to provide the liquid feed to the gas-liquid contact zone at a combined temperature selected to improve olefin stripping. In one aspect of the invention, there is provided a method of recovering a crude aldehyde product stream from a gaseous stream containing aldehyde and unreacted olefin from a hydroformylation system comprising: (a) condensing and separating the gaseous stream in a first condenser stage into (i) a first condenser stage liquid stream at a first temperature and (ii) a first condenser stage gaseous output stream; (b) condensing and separating at least a portion of the first condenser stage gaseous output stream in a second condenser stage into (i) a second condenser stage liquid stream at a second temperature lower than said first temperature of said first condenser stage liquid stream and (ii) a second condenser stage gaseous output stream; (c) feeding the first condenser stage liquid stream and the second condenser stage liquid stream as liquid feed to a gas-liquid contact zone; (d) stripping unreacted olefin from the liquid feed with synthesis gas in said gas-liquid contact zone; and (e) recovering a crude liquid aldehyde product stream from said gas-liquid contact zone having a lower olefin content than the liquid feed to said gas-liquid contact zone. The method is suitably practiced wherein said liquid feed temperature is 68° C. or above, or wherein said liquid feed temperature is 70° C. or above. The first condenser stage liquid stream may be at a temperature of 70° C. or above such as wherein the first condenser stage liquid stream is at a temperature above 75° C. or wherein the first condenser stage liquid stream is at a temperature above 80° C. The second condenser stage liquid stream may be at a temperature of 70° C. or below such as wherein the second condenser stage liquid stream is at a temperature of 65° C. or below or wherein the second condenser stage liquid stream is at a temperature of 60° C. or below.

In practicing the inventive method, the ratio of unreacted olefin to aldehyde in the crude liquid aldehyde product stream may be less than 2 g olefin/kg aldehyde such as wherein the ratio of unreacted olefin to aldehyde in the crude liquid aldehyde product stream is less than 0.55 g olefin/kg aldehyde. At least a portion of the second condenser stage gaseous output stream may be recycled to a hydroformylation reactor and/or at least a portion of the first condenser stage gaseous output stream is provided to a hydroformylation vent reactor. The process may further comprise condensing and separating at least a portion of the second condenser stage gaseous output stream in a third condenser stage into (i) a third condenser stage liquid stream and (ii) a third condenser stage gaseous output stream and feeding the third condenser stage liquid stream with the first condenser stage liquid stream and the second condenser stage liquid stream to the gas-liquid contact zone. In such cases, at least a portion of the second condenser stage gaseous output stream or the third condenser stage gaseous output stream may be recycled to a hydrofromylation reactor. The process may still further comprise condensing and separating at least a portion of the third condenser stage gaseous output stream in a fourth condenser stage into (i) a fourth condenser stage liquid stream and (ii) a fourth condenser stage gaseous output stream and feeding the fourth condenser stage liquid stream with the first condenser stage liquid stream, the second condenser stage liquid stream and the third-stage condenser stream to the gas-liquid contact zone. Optionally, at least a portion of the second condenser stage gaseous output stream or the third condenser stage output stream or the fourth condenser stage output stream is recycled to a hydroformylation reactor.

In another aspect of the invention, there is provided the improvement comprising a multi-stage condensation system for providing liquid feed to the gas-liquid contact zone including condensing and separating the gaseous reactor output stream in a plurality of successive condenser stages into gaseous condenser output streams and liquid condenser output streams having differing temperatures and feeding the liquid condenser output streams as liquid feed to the gas-liquid contact zone. A liquid feed temperature to the gas-liquid contact zone is generally 68° C. or above such as 70° C. or above in preferred cases when practicing the improved method.

What is claimed is:

1. A method of recovering a crude aldehyde product stream from a gaseous stream containing aldehyde and unreacted olefin from a hydroformylation system comprising:
   (a) condensing and separating the gaseous stream in a first condenser stage into (i) a first condenser stage liquid product stream at a first temperature and (ii) a first condenser stage gaseous output stream;
   (b) condensing and separating at least a portion of the first condenser stage gaseous output stream in a second condenser stage into (i) a second condenser stage liquid product stream at a second temperature lower than said first temperature of said first condenser stage liquid stream and (ii) a second condenser stage gaseous output stream;
   (c) feeding at least both of the first condenser stage liquid stream and the second condenser stage liquid stream as liquid feed to a gas-liquid contact zone in order to adjust a liquid feed temperature to the gas-liquid contact zone;
   (d) stripping unreacted olefin from the liquid feed with synthesis gas in said gas-liquid contact zone; and (e) recovering a crude liquid aldehyde product stream from said gas-liquid contact zone having a lower olefin content than the liquid feed to said gas-liquid contact zone.

2. The method according to claim 1, wherein the liquid feed temperature to the gas-liquid contact zone is at a temperature intermediate the first temperature of the first condenser stage product stream and the second temperature of the second condenser stage product stream.

3. The method according to claim 1, wherein said first condenser stage liquid stream and said second condenser stage liquid stream are combined prior to providing them to the gas-liquid contact zone.

4. The method according to claim 1, wherein the liquid feed temperature is between 68° C. and 85° C.

5. The method according to claim 1, wherein the first condenser stage liquid stream is at a temperature of from 70° C. to 105° C.

6. The method according to claim 1, wherein the second condenser stage liquid stream is at a temperature of from 50° C. to 70° C.

7. The method according to claim 1, wherein the first condenser stage liquid stream and the second condenser stage liquid stream are supplied to the gas-liquid contact zone without external heating.

8. The method according to claim 1, wherein the ratio of unreacted olefin to aldehyde in the crude liquid aldehyde product stream is less than 1 g olefin/kg aldehyde.

9. Apparatus for recovering a crude aldehyde product stream from a gaseous stream containing aldehyde and unreacted olefin withdrawn from a hydroformylation reactor comprising:

(a) a plurality of successive condenser stages including a first and last condenser stage, each of which condenser stages is adapted for condensing and separating the gaseous stream into a liquid product stream and a gaseous output stream thereby generating a (i) a plurality of staged liquid product streams at successively lower temperatures and (ii) a plurality of staged gaseous output streams at successively lower temperatures;

(b) a gas-liquid contact zone ducted directly to said plurality of staged liquid product streams in order to receive said plurality of staged liquid product streams in order to adjust a liquid feed temperature to said gas-liquid contact zone, said gas-liquid contact zone being configured and adapted to strip unreacted olefin from the liquid feed with synthesis gas in said gas-liquid contact zone as well as provide a crude liquid aldehyde product stream from said gas liquid contact zone having a lower olefin content than the liquid feed.

10. The apparatus according to claim 9, wherein the liquid feed temperature to said gas-liquid contact zone is at a temperature below a temperature of the first condenser stage liquid product stream and above a temperature of the last condenser stage liquid product stream.

11. The apparatus according to claim 9, wherein said plurality of successive condenser stages consists of two successive condenser stages.

12. The apparatus according to claim 9, wherein said plurality of successive condenser stages consists of three successive condenser stages.

13. The apparatus according to claim 9, wherein said plurality of successive condenser stages consists of four successive condenser stages.

14. The method according to claim 1, wherein the olefin is propylene and the aldehyde product is butyraldehyde.

15. The method according to claim 2, wherein the olefin is propylene and the aldehyde product is butyraldehyde.

16. The method according to claim 3, wherein the olefin is propylene and the aldehyde product is butyraldehyde.

17. The method according to claim 4, wherein the olefin is propylene and the aldehyde product is butyraldehyde.

18. The method according to claim 1, wherein the olefin is ethylene and the aldehyde product is propionaldehyde.

19. The method according to claim 2, wherein the olefin is ethylene and the aldehyde product is propionaldehyde.

20. The method according to claim 3, wherein the olefin is ethylene and the aldehyde product is propionaldehyde.

* * * * *